United States Patent [19]

Shonfeld et al.

[11] Patent Number: 5,562,623
[45] Date of Patent: Oct. 8, 1996

[54] SINGLE-USE SYRINGE ASSEMBLY INCLUDING SPRING CLIP LOCK AND PLUNGER

[75] Inventors: David Shonfeld, Great Neck; Joel S. Schoenfeld, Woodbury, both of N.Y.

[73] Assignee: Univec, Garden City, N.Y.

[21] Appl. No.: 232,749

[22] Filed: Apr. 25, 1994

Related U.S. Application Data

[63] Continuation-in-part of Ser. No. 195,302, Feb. 14, 1994.

[51] Int. Cl.[6] ............................. A61M 5/50; A61M 5/315
[52] U.S. Cl. ........................................ 604/110; 604/218
[58] Field of Search ............................. 604/110, 195, 604/218, 220, 263

[56] References Cited

U.S. PATENT DOCUMENTS

| | | |
|---|---|---|
| 4,013,073 | 3/1977 | Cunningham . |
| 4,022,206 | 5/1977 | Hilleman et al. . |
| 4,367,738 | 1/1983 | Legendre et al. . |
| 4,386,606 | 6/1983 | Tetinyak et al. . |
| 4,391,272 | 7/1983 | Staempfli . |
| 4,391,273 | 7/1983 | Chiquiar-Arias . |
| 4,493,703 | 1/1985 | Butterfield . |
| 4,731,068 | 3/1988 | Hesse ........................ 604/110 |
| 4,781,684 | 11/1988 | Trenner . |
| 4,909,791 | 3/1990 | Norelli . |
| 4,952,206 | 8/1990 | Ibanez et al. . |
| 4,961,728 | 10/1990 | Kosinski ..................... 604/110 |
| 4,969,877 | 11/1990 | Kornberg . |
| 4,973,310 | 11/1990 | Kosinski ..................... 604/110 |
| 4,979,943 | 12/1990 | Trenner . |
| 4,982,842 | 1/1991 | Hollister . |
| 5,000,737 | 3/1991 | Free et al. .................. 604/110 |
| 5,021,047 | 6/1991 | Movern ...................... 604/110 |
| 5,062,833 | 11/1991 | Perler ........................ 604/110 |
| 5,067,942 | 11/1991 | Jaffee et al. . |
| 5,120,314 | 6/1992 | Greenwood ................ 604/110 |
| 5,151,088 | 9/1992 | Allison et al. . |
| 5,183,966 | 2/1993 | Movern . |
| 5,205,825 | 4/1993 | Allison et al. ............. 604/110 |
| 5,222,942 | 6/1993 | Bader ........................ 604/110 |
| 5,259,840 | 11/1993 | Boris ......................... 604/110 |
| 5,290,235 | 3/1994 | Polybank et al. . |
| 5,344,403 | 9/1994 | Lee ............................ 604/110 |

Primary Examiner—John D. Yasko
Assistant Examiner—Adam J. Cermak
Attorney, Agent, or Firm—Levisohn, Lerner, Berger & Langsam

[57] ABSTRACT

A single-use syringe is provided with a rod-like plunger having a plurality of frusto-conical ratchet teeth. A radially resilient locking spring clip having a circumferential opening, dangles on the ratchet teeth of the plunger. The original location of the spring clip on the plunger determines the maximum dosage which can be administered by the syringe. In use, a first withdrawal of the plunger allows medication to be drawn into the barrel of the syringe. The spring clip glides, by radial flexing, over the surface of the ratchet teeth during plunger withdrawal. The spring clip is maintained in relative position along the sidewall of the barrel by outwardly directed contact points which embed into the interior sidewall of the barrel. During administration of the medication previously drawn into the barrel, the spring clip moves along with the plunger since an interiorly directed camming tooth of the clip mechanically cooperates with the base of a ratchet tooth of the plunger. The clip is thus carried along with the plunger during distal/dispensing movement. A second use of the syringe is blocked once the spring clip has been moved to its full distal position. The tensile strength of the plunger is less than the embedding force of the locking clip to the sidewall of the barrel so that, after a full distal movement of the plunger, a second forced attempt of proximal movement will break the plunger.

27 Claims, 12 Drawing Sheets

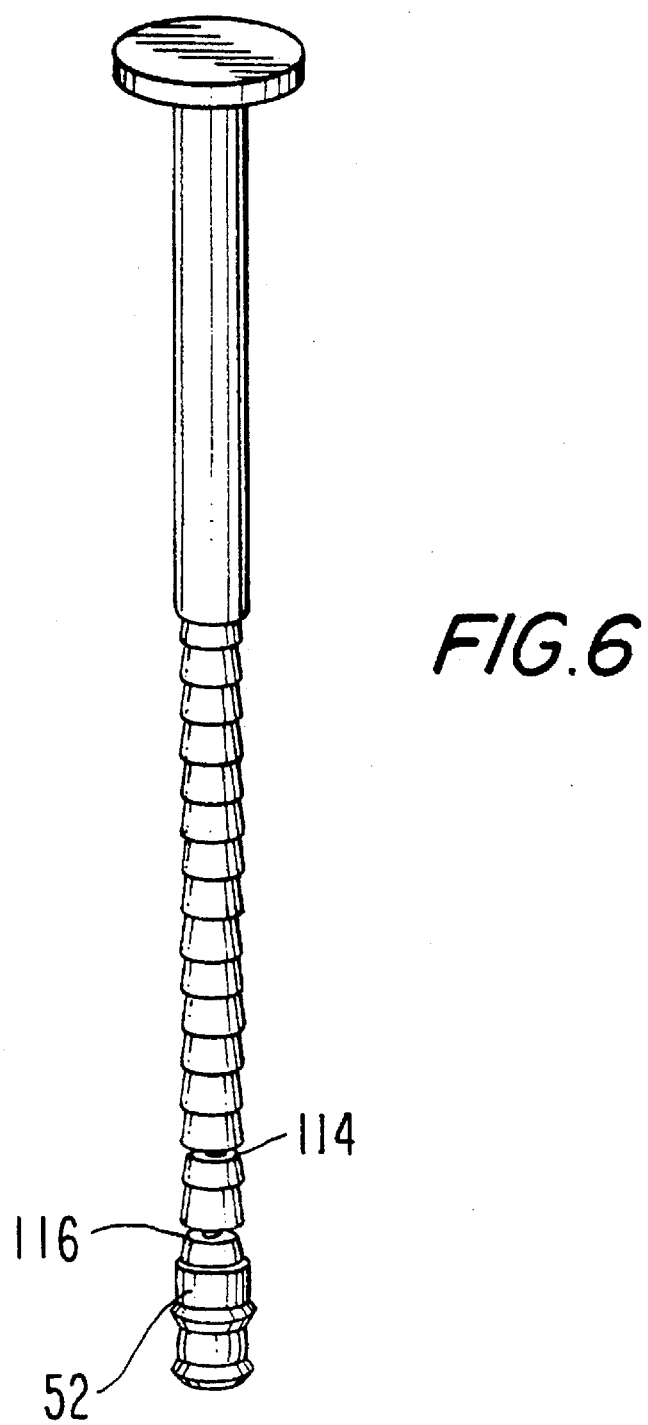

SINGLE-USE SYRINGE ASSEMBLY INCLUDING SPRING CLIP LOCK AND PLUNGER

RELATED APPLICATIONS

This is a continuation-in-part application of application Ser. No. 08/195302, filed Feb. 14, 1994, entitled Single-Use Syringe Assembly. Said application is incorporated herein by reference as if fully presented.

BACKGROUND OF THE INVENTION AND DESCRIPTION OF THE PRIOR ART

This invention relates generally to hypodermic needles and syringes, and more particularly the invention relates to a spring clip lock which can be used to convert a plastic hypodermic syringe into a single-use, difficult to reuse, inexpensive syringe made of already medically approved material. For the purposes of this invention the term single-use means that the maximum dosage placed into the syringe can only be administered one-time. The syringe, however, can administer medication multiple times, each time, however, delivering only a portion of the full medication capable of being drawn into the syringe by a single, full proximal drawing of the plunger rod. For short hand notation, the term single- use means and includes one or more possible uses, with each use delivering less dosage than the maximum. The cumulative total of delivered dosages obtained by all uses can not exceed the maximum dosage drawn into the syringe by a single, distal reciprocation of the plunger rod. The syringe is truly a one-time use syringe when the maximum dosage of the syringe (determined by the barrel capacity and/or the position of the spring clip on the plunger) is fully administered in its first usage. If that occurs, the spring clip is moved to its full distal position and all reuses are blocked. Where less than maximum is delivered on the first or succeeding dosage deliveries, the succeeding dosages administered are necessarily less than the maximum. There can be only one full distal movement of the plunger rod, to administer medication. In this manner, the device is a single-use syringe. The safe, one-time use and subsequent disposal of hypodermic needles and syringes are immediate concerns in the medical and health professions. Accidental needle stick injuries following use of a syringe pose a significant risk to patients, physicians and nurses. The risk is a source of great anxiety due to the current HIV and hepatitis infection concerns of the general public. Thus, extreme care must be taken in the safe handling and disposal of used needles and syringes. Toward this end, the present invention represents a single-use needle and syringe assembly. After the needle and syringe (hereinafter collectively referred to as the syringe) are once used, the mechanism of the present invention precludes further uses. It will, therefore, be more likely properly discarded than if further use were possible. Patient to patient cross contamination and drug user to drug user cross contamination are eliminated.

The present invention is compact and, therefore, is capable of being implemented into syringes of extremely small size barrel capacity including syringes capable of administering dosages as low as to 0.1 cc. The prior art, on the other hand, as will be more fully explained hereinafter, cannot be easily and/or economically downsized while maintaining the effectiveness of the one-time use only mechanism and, therefore, they have not been commercially introduced in sizes smaller than standard 3 cc syringe bodies. The axial location of the locking mechanism in the syringe barrel in the prior art single-use syringes was the means for limiting a 3 cc conventional syringe to a maximum 1 cc dosage. However, it is clearly desired to have smaller maximum dosage syringes where the size of the syringe, not only the location of the clip, determines the maximum dosage capacity. It should be appreciated, however, that the present invention can also be adapted for use with 3 cc or other maximum dosage syringe barrels and, yet, the present invention has particular applicability to syringes of low dosage capacity even those as low as 0.1 cc capacity.

It is generally recognized that a low cost syringe is essential to meet the needs of less developed countries and to contribute to the reduction of health costs everywhere. A low cost would mitigate syringe re-use now encountered with multiple-use disposable syringes. The cross contamination resulting from patient to patient reuse of the same syringe would be obviated by a single-use syringe. It would also reduce patient anxiety resulting from suspected potential infection from syringe use.

The present invention provides a simple and inexpensive to manufacture mechanism for limiting the usage of a syringe (with or without needle) to one-time or single-use only. The syringe is intended to be assembled at the manufacturing facility and provided to the physician (or nurse, patient, etc.) for use. The user fills the syringe with the appropriate medication in the conventional manner, i.e., by withdrawing the plunger with respect to the cylindrical barrel of the syringe, thereby drawing medication through the needle tip and into the chamber of the barrel. Then, again, using conventional technique, the needle is inserted to pierce the patient's skin. The plunger is manually moved with respect to the cylindrical barrel thereby forcing a piston toward the distal end of the syringe. The piston forces the medication out through the needle tip.

During the dosage administration portion of the procedure, according to the present invention, as will be more fully explained hereinafter, a locking spring clip travels along with the plunger shaft and, when it reaches the distal position, locking or contact points are held against the interior sidewall of the cylindrical barrel with the piston abutting the base of the locking spring clip. A second attempted retraction of the plunger with respect to the cylindrical barrel of the syringe is blocked. Thus, no further medication can be pulled into the syringe and, therefore, the syringe is incapable of being used a second time. A simple, inexpensive single-use syringe is provided. The locking mechanism, precluding reuse, is automatic, i.e., it operates to block reuse without a conscious operation by the user to engage its operation.

The design of an economically producible syringe assembly having the feature of single-use and whose safety or one-time use operation is difficult to defeat has been the subject of numerous patents and efforts. Such a syringe should be easy to manufacture and assemble, function in a standard manner, be able to deliver different volumes of fluid, utilize materials which are universally approved for medical use, preferably require standard equipment to manufacture such as used for making syringes in current use, and, importantly, be low in cost.

The present invention accomplishes the above objects by utilizing a new and unique plunger in association and in combination with a new and unique spring locking clip. The plunger comprises a plurality of cylindrical ratchet teeth. The spring clip is located by the manufacturer at a particular location on the plunger so as to limit maximum dosage of the syringe. In addition, the use of this new plunger and spring clip blocks reuse of the syringe. The construction can be incorporated into syringes of even 0.1 cc size without any loss of efficiency or safety. The operating mechanism of the present invention allows extremely small volumetric capacity of syringes to be manufactured, without loss of performance. In contrast, the locking mechanisms of prior art single-use syringes operate in different manners and, therefore, very small volume syringes cannot be manufactured. The present invention is economical to manufacture, has tamper-proof features, administers medication using conventional techniques, is made of medically approved materials, and can be made with standard equipment.

It is a feature of the present invention to provide the thumb-contacting portion of the syringe plunger as a break-apart disc such that, after use, the user of the syringe can simply bend or twist and remove the thumb-contacting disc and, thereby, further disable the syringe from a subsequent reuse. The ability of the thumb-contacting portion of the plunger shaft to become disengaged from the syringe also serves as a means for tracking inventory of the syringes.

It is another feature of the present invention to provide another mechanical locking mechanism. This feature, as well, blocks a second use of the syringe. It engages, however, only when the user deliberately desires to do so, by fully reciprocating the plunger to its maximum distal position. To effect this mechanical lock, the plunger and the thumb-contacting disc portion must be pushed fully toward the distal end of the syringe. When moved as described, the thumb-contacting disc portion and the plunger are locked (incapable of being withdrawn to draw in additional medication) by the interaction of an annular male dove-tail of the plunger which cooperates with an annular female dove-tail of the barrel. Here, too, a safety mechanism is provided to prevent reuse of the syringe.

DESCRIPTION OF THE PRIOR ART

The various approaches described in the patent literature and in other publications have generally described various mechanisms to providing single-use syringes, without reference to geometric limitations such as the minimum total volume such a syringe can contain. It is clear that some minimum contained volume limit exists for single-use syringes which depend not only on the design, but also on limitations on produceability resulting from small dimensions. It is the present practice, where small quantities of medication are to be injected, to prefer the use of syringes of reduced total volume rather than limiting the motion of a larger capacity device as both the accuracy and ease of use are thereby enhanced. The present invention, in contrast to the prior art, uses an entirely different mechanism and operating forces to block syringe reuse. Construction of syringes of extremely small volumetric capacity can thus be achieved.

Safety syringes have been made, in the past, which provide some degree of protection against accidental needle injury. The designs require relatively complex mechanisms or are relatively bulky. Often, they have been relatively expensive to manufacture. Most of the prior art single-use limiting mechanisms are intended for use with the standard X-shaped plunger shaft of conventional syringes. The present invention, on the other hand, contemplates the use of an entirely new plunger shaft which is, in basic form, a rod comprised of ratchet teeth. Moreover, activation of the safety features of the prior art mechanisms can sometimes fail or be intentionally disengaged. It is believed that the present invention is more effective at preventing syringe reuse.

Of particular importance, however, as mentioned, the present invention is believed extremely efficient, inexpensive and capable of being incorporated into syringes of dimensions suitable for even 0.1 cc maximum dosage capacity. In this manner, the device can be incorporated into very small dosage syringes. This is highly desirable. In contrast, prior art single-use or "safety" syringes seem incapable or difficult to reduce in size. They have not been commercialized in 0.1 cc maximum dose capacity but, rather, the manufacturers use standard larger barrel syringes (3 cc, for example) and limit the degree of movement of the plunger shaft to limit the maximum dosage. It is a specific object of the present invention to provide a single-use syringe in a maximum capacity as low as 0.1 cc.

Previous approaches to the design of single-use disposable plastic syringes may be classified as follows:

(a) Locking of the plunger after delivery;

(b) Disengagement of the plunger;

(c) Withdrawal of the needle into the syringe barrel after dose delivery;

(d) Physical destruction of some portion of the syringe;

(e) Chemical means to disable the syringe after first use; and (f) The use of supplementary means such as sleeves to prevent reuse of the syringe while simultaneously offering pin-prick protection.

A syringe of the present invention utilizes a mechanical method to lock the plunger from further use by a novel spring lock clip mechanism, as described below.

Prior art locking mechanisms generally operated on conventional X-shaped plungers, and, in some cases, on a cylindrical plunger. In use of the X-shaped plunger, the plungers are maintained in axial alignment with the axis of the barrel by the edges of the plunger. In the use of a locking device on a cylindrical plunger, the locking devices were symmetrical, extending entirely around the plunger. Thus, these plungers were also maintained in axial alignment with the barrel. The axial alignment between barrel and plunger in the prior art X-shaped and locking clip devices and those cylindrical plungers with surrounding locking clips, preclude reducing the volume capacity of the syringe.

The present invention, in contrast, uses a new locking mechanism on a cylindrical plunger. The structure and manner of operation of the present inventive spring locking clip results in a radial displacement of the plunger within the barrel. This non-axial alignment between plunger and barrel allows for the manufacture of single-use syringes in much smaller volumetric capacity than previously available.

U.S. Pat. No. 4,386,606 utilizes sharp edges on a plunger, cam or barrel to securely lock the syringe having an X-shaped plunger.

U.S. Pat. No. 4,367,738 describes a non-reusable syringe utilizing a plurality of stiff, flexible spikes.

U.S. Pat. No. 4,731,068 shows rigidly secured spider-like barbs mounted on a cylindrical plunger to lock the syringe after delivery to prevent reuse.

U.S. Pat. No. 4,952,206 uses barbs to allow a washer located within a valve to impede fluid flow after drug delivery.

U.S. Pat. No. 4,961,728 utilizes non-parallel barbs on a locking element for an X-shaped plunger.

U.S. Pat. No. 4,979,943 provides a reversible stop member which permits plunger motion in one direction only.

U.S. Pat. No. 5,000,737 utilizes a circular or fluted, barbed lock which engages an X-shaped plunger.

U.S. Pat. No. 5,021,047 and U.S. Pat. No. 5,138,466 utilizes locking barbs which completely surround the plunger. The motion of the lock as it relates to the plunger causes it to flex in an axial mode as it is forced over the ratchet teeth.

U.S. Pat. No. 5,205,825 utilizes an insertable clip to lock X-shaped plungers.

WO 89/00432 utilizes a ratchet plunger and ratchet wall to prevent reuse.

U.S. Pat. No. 5,000,737 relates to a single-use disposable syringe. The figures reveal a device adapted for placement over X-shaped conventional plunger shafts. Outwardly directed points of the claimed flute are intended to dig into the interior cylindrical sidewall or surface of the needle barrel so as to prevent movement of the disk with respect to the barrel when the plunger shaft is moved in the proximal direction (the direction for drawing medication into the barrel). Inwardly directed edges are adapted to engage the adjacent walls of the X-shaped plunger so that the device travels along with the plunger when the plunger is moved distally (to dispense the medication). FIGS. 8–16 of the identified patent relate to the claimed invention of the '737 patent. That device is intended to be held in a quadrant of the syringe barrel defined by the X-shaped plunger member. It is described, according to the patent, as "elongated" i.e., its length is greater than its width dimension.

The present invention, on the other hand, as will be more fully explained, is not elongated. It is compact and easily fabricated for small-sized syringes. It is less expensive to manufacture and believed far simpler to fabricate. It will not fail in the event of axial misalignment and, indeed, operates by axial nonalignment. By being constructed and operating in this manner, the volume of the syringe can be made far smaller than that capable of construction with prior art syringes. Furthermore, the present invention contemplates use in connection with a new plunger. The locking spring as now presented is not confined within a quadrant of the barrel, defined by an X-shaped plunger, but, rather, it extends only partially around a new cylindrical plunger on the inside of the barrel. This provides more uniform pressure of the locking mechanism against the interior sidewall of the barrel and ensures that the present invention is useful in preventing reuse of a one-time used syringe. The manner of operating, i.e., the plunger being pushed off center or out of axial alignment with respect to the axis of the syringe barrel has vast advantages over the prior art. The '737 patent also shows a disc-like member which operates in a manner quite similar to the flute claimed in the '737 patent. It, too, is intended for use with conventional X-shaped plungers. It, too, seems difficult to downsize for manufacture of 0.1 cc syringes.

U.S. Pat. No. 5,151,088 also relates to a safety needle and syringe assembly. A disposable syringe and needle assembly is depicted and described having a small rigid retractable needle shield provided in the syringe. Following an injection, the needle shield is extended into a locked position covering the needle. The shield only assumes the locked position when the user presses the syringe plunger past the zero volume point. Thus, if the user does not accidentally or consciously do so, this device will not block reuse. It is an object of the present invention to automatically prevent reuse of a syringe so as to eliminate person to person contamination, a consequence of needle reuse. Automatic engagement of the locking mechanism is not accomplished by the '088 device. Utilizing the invention of the '088 patent, a user, desiring to defeat the mechanism and to reuse the syringe, can avoid engagement of the locking mechanism by deliberately failing to press the syringe plunger past the zero volume point.

U.S. Pat. No. 5,205,825 (Allison et al.) relates to an insertable element for preventing reuse of plastic syringes. This device, similar to that shown in the Free et. al. '737 patent, provides a locking mechanism intended to be retrofitted into existing conventional syringes by inserting the same onto the standard X-shaped plunger within a plastic cylindrical barrel of the syringe. The same comments previously made with respect to the device of the Free et. al. patent are equally applicable to the Allison et. al. patent i.e., with respect to its inability to be made effectively and efficiently in a smaller maximum dose size and, further, the advantages achieved by the present invention, a consequence of the nonalignment of the plunger with the axis of the cylindrical barrel.

U.S. Pat. No. 5,067,942 relates to a single-use hypodermic needle, as well. When the needle assembly and the syringe are assembled, two separable tabs held within a basket force the sheath to retract and expose the port in the needle whereby a fluid can flow through the needle. Upon disassembly of the needle syringe, the tabs separate from the basket and are effectively destroyed for further use in retracting the sheath. The present invention is believed far simpler, less expensive to manufacture, automatic and is more easily adapted for smaller sized syringes then that shown in the '942 patent.

A number of safety syringe designs incorporating needle covers have also been proposed. U.S. Pat. Nos. 4,909,791 and 4,982,842 employ jaw members pivotally mounted onto a syringe barrel for covering a needle after use.

U.S. Pat. No. 4,969,877 discloses a syringe assembly in which an outer casing is provided around an inner chamber or syringe portion which slides on the outer casing to an operational position and to a retracted position at the forward and rearward ends of the outer casing, respectively.

U.S. Pat. No. 4,013,073 discloses a collapsible single-use syringe wherein the interior of the collapsible wall is constructed such that when the walls are pressed together to discharge the medication, they interlock and therefore render the device incapable for reuse.

U.S. Pat. No. 4,022,206 shows a method and apparatus for storing and delivering a vaccine in a single dose prepackaged system. No provision is made for rendering the unit mechanically incapable for subsequent use.

U.S. Pat. No. 4,391,273 shows a rigid type syringe including a pin which is attached to the piston which penetrates the bottom wall of the cylinder after the injection has been completed. This, too, renders the syringe inoperable after a first time use. In an alternative embodiment, the patent shows a knife blade which permits movement of the cylinder in a forward direction but the knife serves to cut the sidewall of the cylinder if there is an attempt to recycle the piston or reuse the syringe.

Prior techniques for preventing reuse of needle syringes include various arrangements for locking out the plunger of the syringe after it has been first loaded and then reciprocated to the end of its travel to inject the contents of the syringe. For example, U.S. Pat. No. 4,731,068 discloses a two-part lock construction having a band or sleeve assembled at the injection end of the syringe and dimensioned to be frictionally slidable along the inner wall of the syringe. A spider-like element is mounted in a fixed position on the plunger and has barbed points engaged with the sleeve. When the plunger is first retracted, the spider element and sleeve travel toward the end of the syringe, together with the plunger. When the plunger is depressed toward the injection end, the sleeve remains at the distal end (through frictional engagement with the inner wall) while the spider element travels toward the injection end with the plunger. If a second attempt is made to retract the plunger, the barbs of the spider element, now exposed to the inner wall in the absence of the sleeve, will engage the inner wall of the syringe and prevent a second retraction.

An alternative embodiment shown in the '068 patent has the sleeve slidably supported on the plunger and engaged with the spider element. That element is provided with curved spring-like prongs assembled at the distal end of the syringe. On the first retraction, the sleeve remains engaged with the spider element, and on the first depression, it is moved toward the injection end to expose the prongs of the spider element. An attempt to retract the plunger a second time will be prevented by engagement of the prongs with the plunger. Other devices, for example, U.S. Pat. No. 4,781,684; 4,493,703; 4,391,272 and 4,367,738 provide modifications to the plunger or syringe wall structure. These allow only one way movement of the plunger or lock or disable the plunger after a first depression. They, too, relate to single-use syringes.

U.S. Pat. No. 5,290,235 relates to a non-reusable syringe. In use, a locking member interacts with the guide arrangement of the plunger and the inside surface of the hollow body of the syringe so as to allow a first intake stroke and a delivery stroke but to prevent a second intake stroke of the plunger.

The device shown in the '235 patent generally comprises a conventional syringe with hollow body; an elongated plunger rod extending out of the body for facilitating movement of a piston; the plunger rod having a guide means carrying a locking member, like a plate, with at least one snag projection facing the inside surface of the barrel wherein the guide causes relative pivotal movement of the locking member from a first position where the plunger freely moves in the distal direction to a second position wherein the barb(s) engage the inside wall of the barrel.

The construction of the device of the '235 patent is far more complicated than that of the present invention. The present invention contemplates the use of a simply molded cylindrical, yet ratcheted, plunger shaft, having a spring clip mounted thereon. The original location of the spring clip will determine the maximum volume of the supplied liquid. The device of the '235 patent, in contrast, shows a complicated plunger. It does not seem suitable for mass production. The present invention allows a single plunger rod to be used for a variety of maximum dosage syringes. In the '235 patent, each syringe with a different desired maximum capacity requires a different distance on the plunger between the first face 22 and the stop face 26.

The present invention is extremely easy to fabricate, manufacture and assemble. It is easily capable of use with standard size syringe barrels and, in addition, of commercial importance, it is fully capable of being down-sized for use in connection with syringes having a maximum dosage capacity as low as 0.1 cc. The present invention is fail-safe, i.e., automatic in operation and, in the preferred embodiment, as will be more fully explained, provides multiple lock-out mechanisms thereby ensuring that re-use of a one-time used syringe can not occur. The present invention, furthermore, allows for the selective axial location of the locking spring mechanism on the cylindrical plunger shaft such that maximum dosages can be provided by the manufacturer even though the syringe barrel and plunger can be manufactured in a single size. Thus, location of the locking spring mechanism with respect to the barrel and the plunger, at the time of manufacture, ensures that the administering physician, nurse, technician or user can not administer an overdose of the particular medication. The locking spring mechanism can assume a variety of initial locations at the time of manufacture depending upon location of placement on the plunger, so that there can be economy of manufacture, since only one cylindrical barrel and plunger element need be manufactured. The position of original location of the locking spring mechanism with respect to the plunger determines the maximum quantity of dosage which a particular syringe is capable of administering. Thus, the present invention not only provides a mechanism for ensuring that syringes can not be reused, but, in addition, the locking spring mechanism limits the amount of medication which can be administered for any particular use of that syringe.

The present invention, as will be more fully detailed hereinafter, also provides for a back-up safety mechanism to further disable the syringe after its first time use. This feature however, is not automatic but, rather, requires that the user physically separate the thumb-contacting disc portion of the plunger from the plunger shaft to thereby further mechanically disable the syringe from being used a second time. Removal of the thumb-contacting disc portion serves a secondary purpose of facilitating inventory control since the discs, the remaining portion of the syringe after the bulk has been discarded, can be used to facilitate inventory control.

It is a further object of the present invention to provide yet another lock-out feature preventing the syringe from being used a second time. In this embodiment, a full distal reciprocation of the plunger with respect to the syringe barrel will cause an annular male dove-tail portion of the thumb-contacting disc to engage and mechanically lock into an annular female dove-tail like arrangement of the cylindrical barrel. This locks the disc and shaft fully within the interior of the barrel and prevents movement of the shaft outwardly with respect to the barrel. Blockage of this movement prevents further medication from being withdrawn into the body of the syringe, thereby rendering the device non-reusable.

The geometry of the present invention allows the device to be made in maximum dosages as low as 0.1 cc. This is due to the fact, as will be explained, that the locking device operates radially, i.e., it pushes the plunger rod off axis in the barrel. In this manner of operation, the locking clip need only be a single thickness. It need not surround the plunger rod. As constructed and in operation, the plunger rod, barrel and locking clip can be downsized without loss of function, to a size to deliver medication as low as 0.1 cc maximum dosage. This is not available in the prior art.

SUMMARY OF THE INVENTION.

The present invention relates to a single-use syringe wherein re-use is mechanically blocked. It is an object of the present invention to provide a single-use syringe which is simple in construction, inexpensive to manufacture and automatically prevents re-use. It is a further object of the present invention to provide an inexpensive syringe which is capable of mechanically blocking re-use which syringe can be made of very small dosage capacity. For example, it is a specific object of the present invention to provide a one-time use syringe capable of maximum dosage as low as 0.1 cc.

Another object of the present invention is to provide an inexpensive, spring-like mechanism which, when placed upon a ratcheted plunger shaft, limits the quantity of medication which can be withdrawn into the barrel of the syringe and then administered. The initial location of the locking spring mechanism, with respect to the ratcheted cylindrical shaft, determines the maximum capacity of that particular syringe. Thus, it is a specific object of the present invention to provide a single-use syringe capable of having a variety of maximum dosage capacities dependent upon the location of the spring clip with respect to the plunger shaft. The manufacture of a single size barrel, therefore, provides for economies of manufacture.

It is a further object of the present invention to ensure that a one-time use syringe is provided which can not be easily intentionally disabled. It is also an object of the invention to ensure a one time use syringe which is intended to operate by radial displacement between the plunger and the axis of the barrel of the syringe. This is, in part, accomplished by the use of a new plunger shaft which is basically rod-like and by use of a spring-like clip which radially flexes inwardly and outwardly, locatable on the cylindrical shaft. Non-axial alignment between the cylindrical plunger shaft and the inside barrel wall of the syringe enables the one-time use locking mechanism to be downsized for syringes capable of providing dosages as low as 0.1 cc. It is a specific object of the present invention to provide a one-time use locking mechanism for a disposable syringe which is capable of use on plunger shafts. Eliminating the X-shaped plunger allows the present invention to be more easily made in smaller dimensions. Using the ratcheted plunger rod and the spring locking clip of the present invention eliminates the necessity shown in the prior art, of locking clips substantially surrounding cylindrical plunger shafts. In this manner, very small capacity syringes can be made.

The plunger shaft of the present invention comprises a plurality of cylindrical ratchet teeth. The locking spring, as will be explained, is intended to be initially located on a selected one tooth of the plunger. Thus, the present invention allows for more precise dosage limiting than available with the prior art devices. A mechanical locking between the locking spring and the plunger ensures the maximum dosage in fixed integral amounts whereas the prior art controls maximum dosage by infinitely variable sliding location of a flute along the X-shaped legs of the plunger, not nearly as easy to precisely control.

It is a further object of the present invention to provide a thumb contacting disc portion of the plunger shaft which can be selectively bent or twisted and removed from the plunger shaft after the syringe has been used. In this manner, the thumb-contacting disc portion can be used for keeping track of syringe usage and inventory. Furthermore, removal of the thumb-contacting disc portion of the plunger shaft serves to further disable the syringe, preventing possible re-use.

It is a further object of the present invention to provide another locking mechanism further disabling the syringe from re-use after a one-time intended use. This locking mechanism is accomplished by cooperation of an annular male dove-tail of the thumb-contacting disc portion of the plunger shaft with an annular female dove-tail-like receptacle at the proximal end of the barrel of the syringe. A full reciprocating cycle of the plunger shaft with respect to the cylindrical barrel of the syringe serves to mechanically lock the plunger shaft into its full distal position thereby preventing a second unauthorized or unintended withdrawal of the plunger shaft with respect to the barrel of the syringe.

Another object of the present invention is to provide a mechanism whereby syringes of identical dimensions can be restricted to contain and deliver different dosages, thereby reducing the need for syringes of different sizes.

The present invention is directed to a mechanical means which utilizes a ratchet and spring clip to achieve the above enumerated desirable features. The operation of the syringe assembly relies on a loosely engaging spring clip which allows the syringe to be filled when the plunger is withdrawn. This clip is nearly semi-cylindrical, and has the ability to flex radially, both inwardly and outwardly, and contains barbs outwardly directed so as to be able to position themselves sufficiently independently to conform to variations in barrel diameter due to manufacturing tolerances or imperfections. The present invention also has alignment elements, which function as the locking clip advances toward the needle. The alignment mechanism adds stability when the plunger is attempted to be reused for a second refill as described below. The plunger contains a front seal to provide smooth functioning by applying uniformly distributed force on the embedding barbs during any attempted second withdrawal of the plunger after a first medication delivery.

As the plunger is withdrawn to fill the syringe, the spring locking clip, although stationary in the syringe barrel, is forced to cam over one or more teeth of the ratcheted cylindrical plunger as a result of a radial flexing motion. The clip can accommodate the varying diameter of each tooth of the plunger because it is radially open, being only about semi-cylindrical in shape. During delivery of fluid by the forward motion of the plunger and piston, the clip flexes radially. The clip is carried or urged forward relative to the barrel by the plunger. After injection, with the plunger at its most forward position, the clip prevents any second rearward withdrawal of the plunger since the barbs are embedded into the plastic barrel wall. Any attempt to overcome the resulting friction results in the plunger rod breaking because its tensile strength, reduced by the reduced cross section of the plunger at predetermined locations, is less than the force necessary to overcome the frictional resistance provided by the barbs embedded in the inside wall of the barrel. In another embodiment, a second or more reduced diameter sections of the plunger can be provided to further protect against reuse.

It is an object of the present invention to provide a design which is readily manufacturable by standard molding and assembly methodology at a cost comparable to that currently experienced in the manufacture of disposable plastic syringes.

It is an object of the present invention to achieve smooth operation of the syringe. It is an object of the invention to provide a one-time use syringe which will not jam, particularly for lower volume syringe sizes.

It is a further aim to provide a plunger and locking spring clip in which the mechanism allowing positioning and actuation of the lock function is a consequence of radial flexing of the locking member around the plunger and within the barrel of the syringe.

It is a further object to provide a locking spring clip having flexible, locking or contact points capable of independently interacting with the barrel wall and allowing for variations in barrel diameter.

It is a further object to provide a syringe wherein attempted re-use leads to rendering the syringe inoperable.

It is a further aim to provide secondary fail-safe mechanisms, i.e., complimentary means to provide tamper-proof capability.

It is a further object of the present invention to provide a design offering the above features for syringes capable of precisely delivering as little as 0. 1 cc of liquid.

It is an object to provide the above features within a single syringe having a variable predetermined maximum volume of fluid which can be withdrawn into the syringe.

It is an object of the present invention to achieve the above desired aims utilizing materials which have been approved by official and government regulations.

It is an object of the present invention to allow the syringe to be able to be modified to minimize accidental needle pricks.

It is also an object of the present invention to provide for multiple lock mechanisms to assure syringe disablement by different approaches and to hinder access to the operative locking mechanisms.

It is an object of the present invention to allow varying amounts of fluid to be deliverable with a given barrel diameter.

The objects, features and advantages of the present invention will become apparent from the following detailed description of the preferred embodiment of the invention considered in conjunction with the drawings, as follows:

BRIEF DESCRIPTION OF THE DRAWINGS

FIG. 6 is a side plan view of a second embodiment of a plunger, this version containing two reduced area gaps;

DETAILED DESCRIPTION OF THE DRAWINGS AND THE PREFERRED EMBODIMENT

Figure 1:
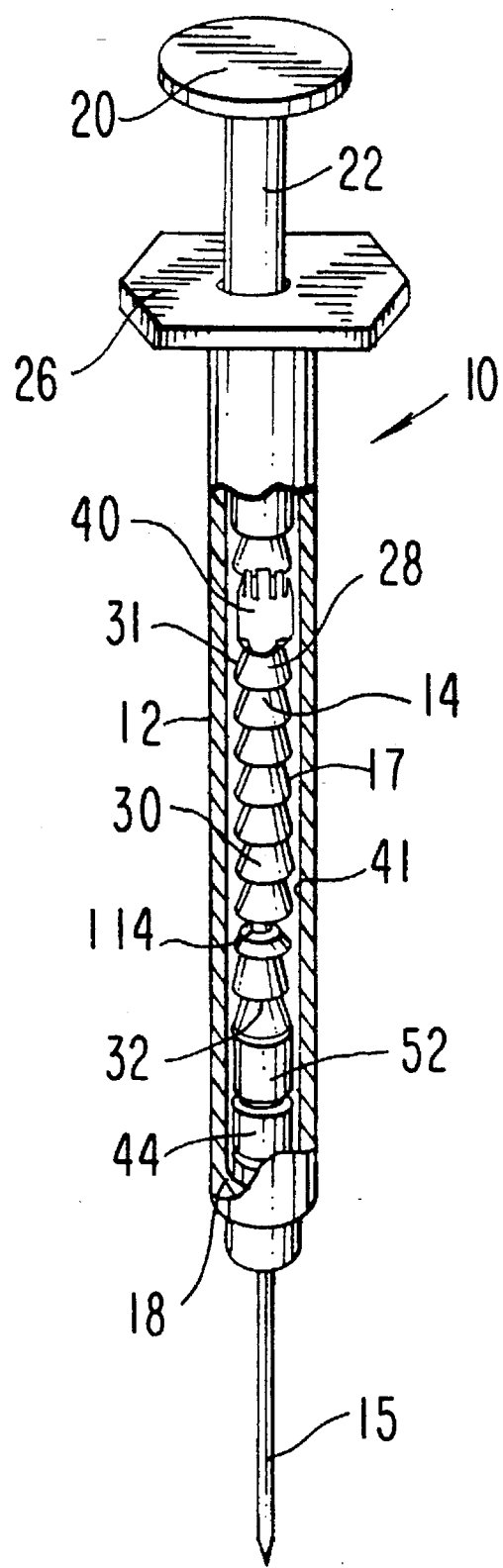
FIG. 1 is a perspective side view of the syringe portion of the present invention showing the locking spring in its initial position, as sold by a manufacturer, dangling on the ratcheted plunger shaft. This Figure shows the syringe of the present invention in its configuration as intended to be distributed to a user for first filling with medication and then subsequent dispensing of the same. The needle extending from the syringe is conventional in configuration.
Figure 2:
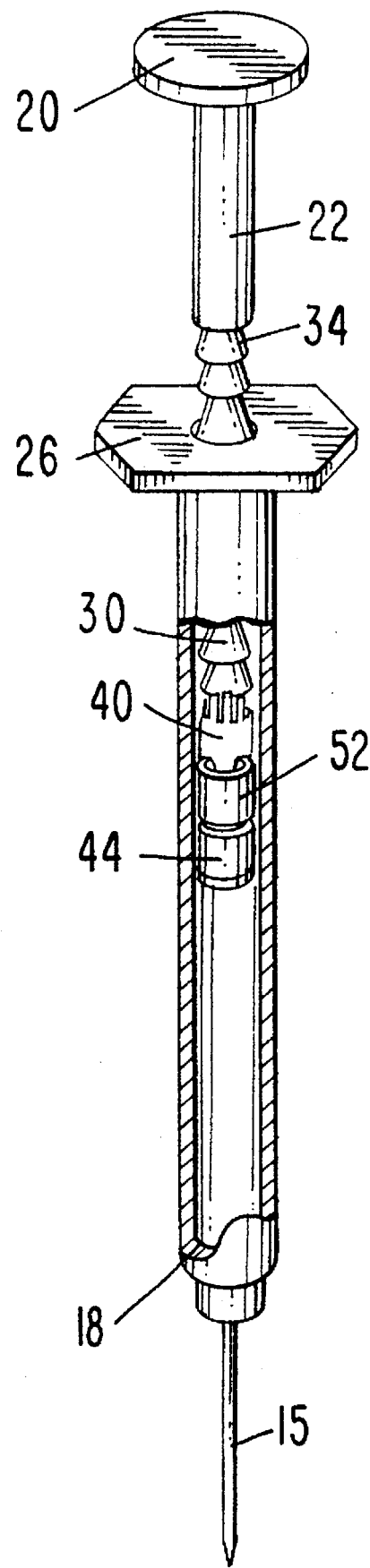
FIG. 2 is a perspective side view of the present invention, in its position after filling with medication and ready to be dispensed.
Figure 3:
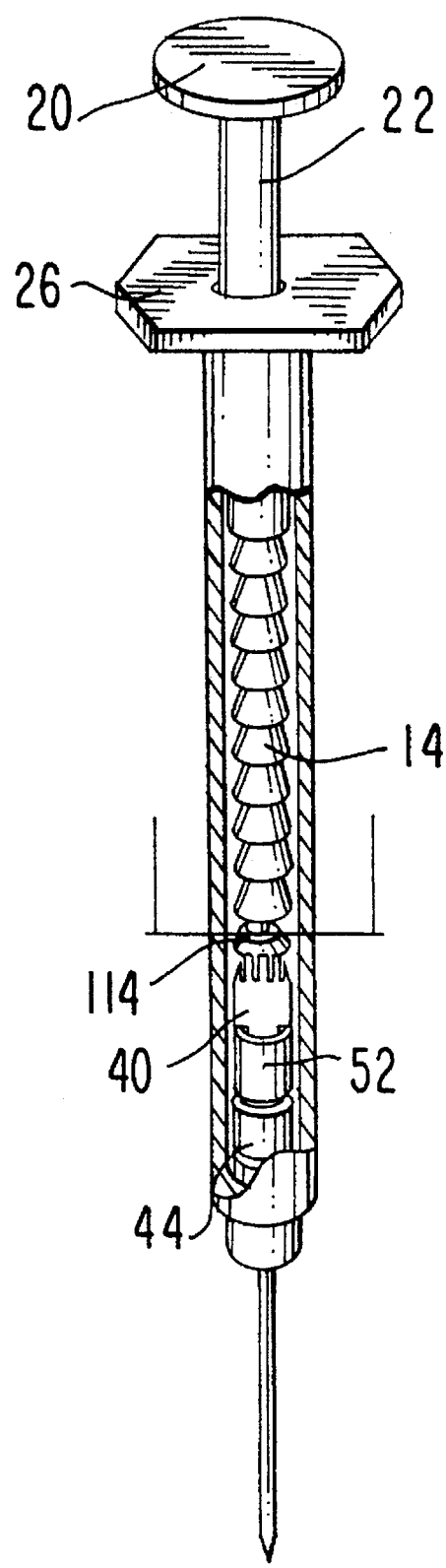
FIG. 3 is a perspective view of the present invention after deliver of the medication, showing the locking spring clip in its most forward or distal position, as carried there by the plunger's ratcheted teeth.
Figure 4:
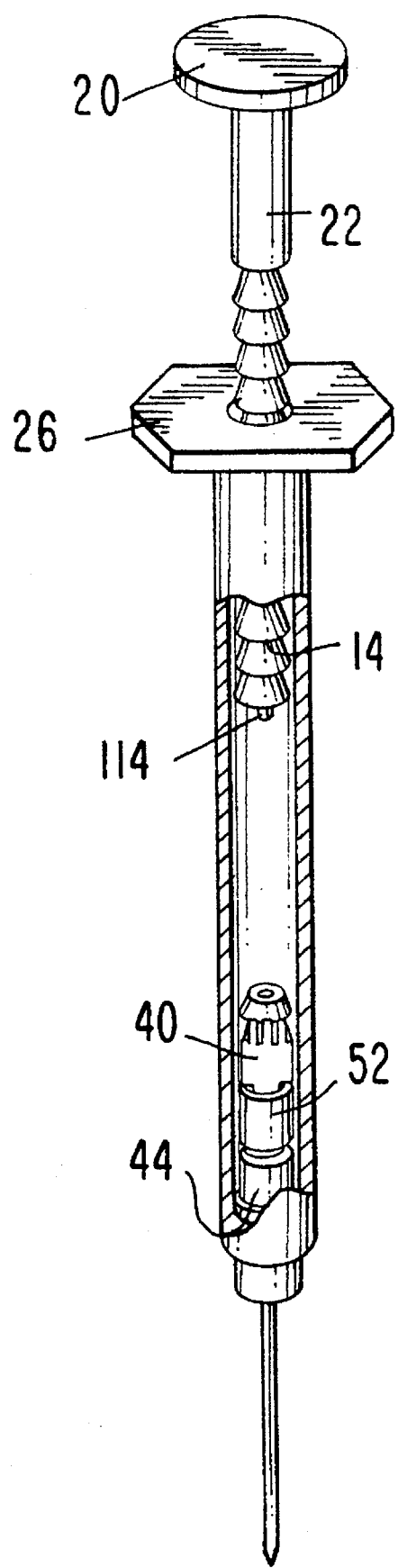
FIG. 4 is a perspective view showing the manner by which the plunger becomes severed, a consequence of a second attempted proximal movement of the plunger.
Figures 5, 5A:
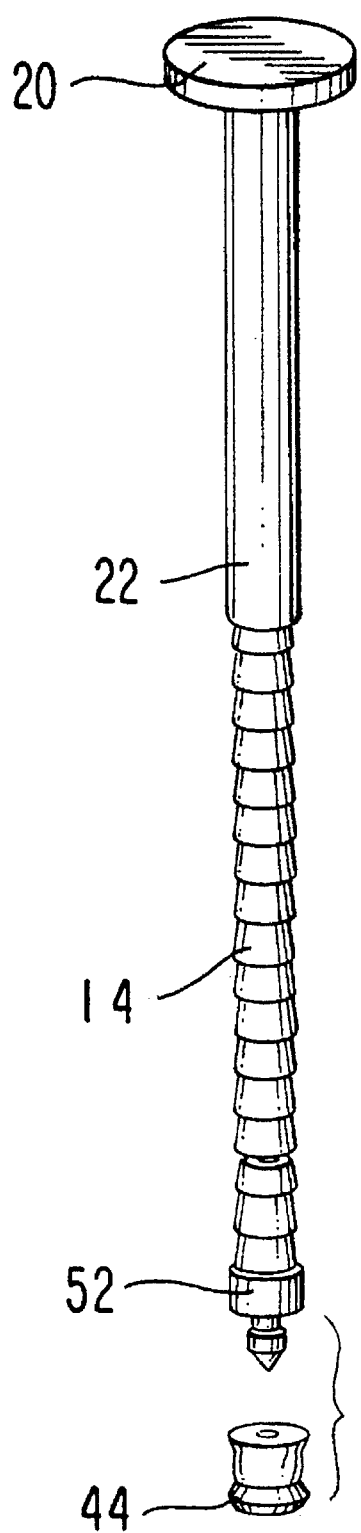
FIG. 5 is a perspective view of the preferred embodiment of the plunger.
FIG. 5a is a perspective view of the resilient insert or piston of the plunger mechanism.

As best seen in the drawings, the present invention, a syringe 10, comprises a main cylinder body 12 and a reciprocating plunger member 14 slidable, received and contained within the cylinder body 12. The preferred material for the cylinder body is a clear medical grade polypropylene which is insoluble and unreactive with most medications and has been FDA approved. The preferred plunger material is medical grade polypropylene modified by the incorporation of a suitable additive so as to provide embrittlement to the resin.

A needle 15 is attached to the distal end of the syringe 10 in a conventional manner. Of course, the syringe can be sold separately from the needle. The details of the construction of the needle and its manner of attachment to the syringe are not believed necessary for a full understanding and appreciation of the present invention. The needle 15 is secured to the tip 18 of the cylinder body 12. For purposes of this description, the end of the cylinder body 12 towards the tip and needle will be referred to as the distal end and direction or motion toward that end is referred to as distal. The other end of the syringe, i.e., the end of the plunger member 14 having the thumb-contacting disc 20 and the finger grips 26 is referred to as the proximal end and direction or motion toward that end is referred to as proximal. As can be seen in the Figures, the thumb-contacting disc 20 is secured to the proximal end of the plunger member 14 and facilitates withdrawal or proximal movement of the plunger member 14 with respect to cylinder body 12 as well as medication dispensing or distal movement of the plunger member 14 toward the tip 18 of the cylinder body 12. The proximal motion draws medication through the needle and into the barrel or chamber of the syringe while distal motion dispenses medication, held in the barrel, through the tip 18 and the needle 15. The medication is dispensed from the cylinder body or barrel by the sliding action of resilient piston 44 against the inner sidewall 17 of the barrel.

Figure 8:
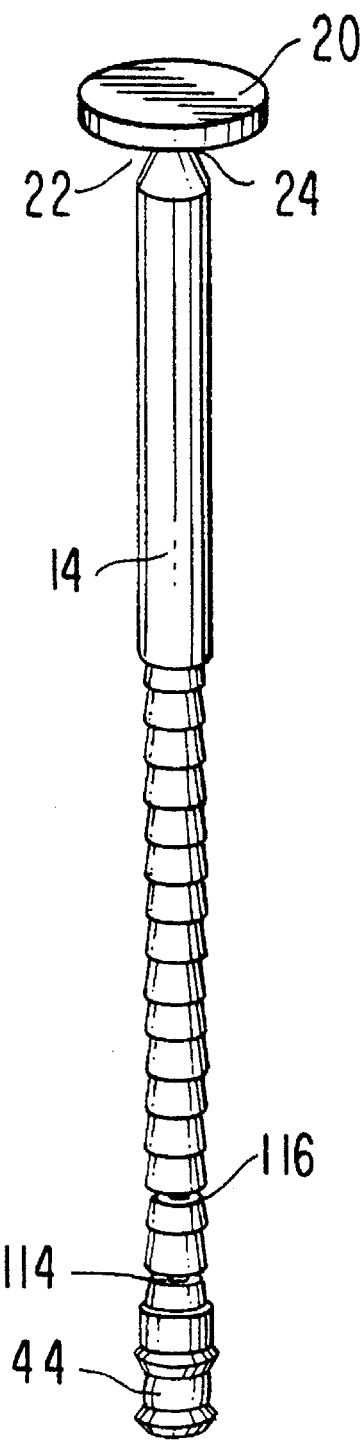
FIG. 8 is a side view of a fourth plunger embodiment containing three reduced areas, one adjacent to the thumb-contacting disc.

The thumb-contacting disc 20 is secured to a segment 22 of the plunger member 14. In the embodiment of the invention shown in FIG. 8, segment 22 is partially frusto-conical and represents a reduced diameter, fracture plane 24. As seen in FIG. 8, the reduced diameter end of segment 22 forms the base for the thumb-contacting disc 20. After use of the syringe the thumb-contacting disc 20 can be bent with respect to fracture plane 24 until the disc breaks apart or separates. Removal of the thumb-contacting disc 20 facilitates further disabling of the syringe, after use, ensuring that the syringe can not be used again since it would be difficult to reciprocate the plunger without the disc 20. The disc 20 serves not only to disable the syringe from further reuse, but also as a convenient, compact inventory control mechanism.

Referring back to FIGS. 1–4, the cylinder body 12 is provided, at its proximal end, with a finger grip or finger support plane 26. It provides a convenient finger support surface for the reciprocation of the plunger member 14 with respect to cylinder body 12 and provides a rest surface for the user's fingers during use.

The plunger member 14 is a rod, in basic configuration. Frusto-conical ratcheting teeth 28 extend over a portion of the length of the plunger member 14. As can be best seen in the Figures, each ratchet tooth 30 comprises an inclined, outwardly extending (from proximal to distal end) camming or inclined surface 31, and is molded to an adjacent ratchet tooth by a base or common plane 32 having an enlarged diameter D1 (for the upper relative tooth) and a reduced diameter D2 (for the lower relative tooth). (see FIG. 3)

Figure 7:
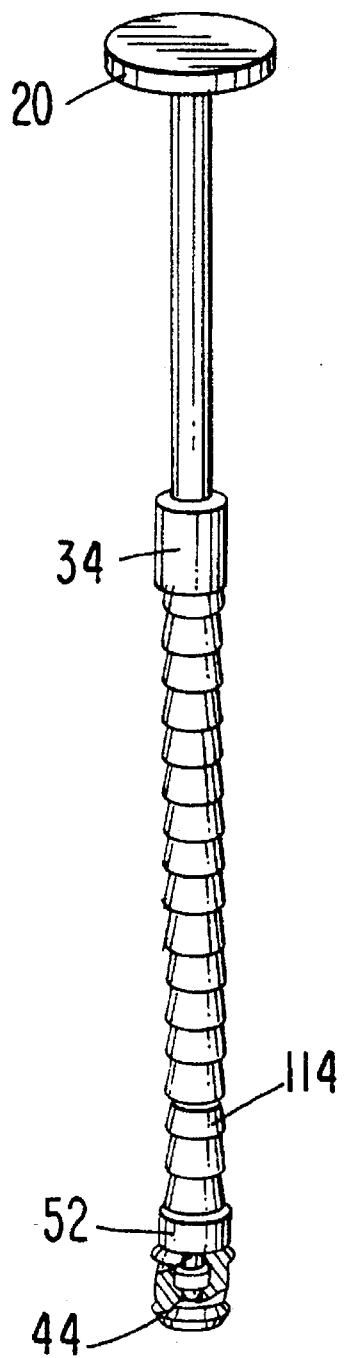
FIG. 7 is a side view of a third plunger embodiment with a single reduced area gap and an enlarged area for preventing tampering.

In the embodiment shown in FIG. 7, a plunger seal 34 encircles plunger member 14 directly above the most proximal ratchet tooth. The plunger seal 34 can be integrally molded or formed with the plunger or, alternatively, it can be a separate resilient component. A close fitting of the plunger seal 34 (or segment 22 of the plunger shown in FIG. 1) to the barrel limits access to the spring locking clip and makes the device tamper proof. The closeness of parts between seal 34 (and/or segment 22) and the inner sidewall 17 of the barrel is represented by small gap 41. The plunger seal 34 or segment 22 has an outside diameter larger than the diameter D1 of the ratchet teeth and, in the embodiment of FIG. 7, the plunger seal 34 has a diameter about that of the interior sidewall 17 of the barrel. The plunger seal provides a barrier between the outside of the syringe and the ratchet teeth so that foreign objects cannot enter between the plunger member 14 and the inner sidewall 17 of the cylinder body 12. Thus, the plunger seal 34 or segment 22 serves as a sealing device to prevent unauthorized access to the locking spring 40 so that it can not be disabled from its intended use. In an alternate embodiment, the plunger seal 34 is rubber and physically contacts and is, at least in part, partially compressed by the relative diameter of the inner sidewall 17.

The distal end of the plunger member 14 comprises a piston or fluid-pushing sealing member 44. It is preferably made from a rubber-like substance, partially compressible material. Preferably, the piston is a synthetic medically approved rubber. Here, again, the piston 44 may be integrally molded or formed with the plunger or a separate rubber component. As seen in FIGS. 5, 5a and 6-8, the piston can be attached to the distal end of the plunger by a blind hole which is forcibly mounted on a frusto-conical cone, seen in FIG. 7. This secures the rubber piston to the plunger. The piston 44 has a diameter, when radially compressed by the sidewall 17 of the barrel, substantially equal to the diameter of the inner sidewall 17 and provides a sliding, yet sealing, contact therebetween. When the plunger member 14 is reciprocated within the cylinder body 12, all fluid (distal of the piston 44) will be pushed through the tip 18 and, therefore, through the needle 15. The sealing member 44 also prevents any medication or fluid from entering into the cavity above (or proximal) to it. Piston 44, of course, travels along with the plunger member 14 and is physically secured thereto.

Adjacent to the proximal end of piston 44 is an enlarged plunger portion seal section 52 which, similar to plunger seal 34 or segment 22, provides a safety seal to prevent unauthorized access to the ratchet teeth 28 and the locking spring 40. It, too, prevents a paper clip, a knife point, etc. from gaining access into the space proximal of the piston. The diameter of section 52 is about that of the interior sidewall of the cylinder body 12.

Figure 9:
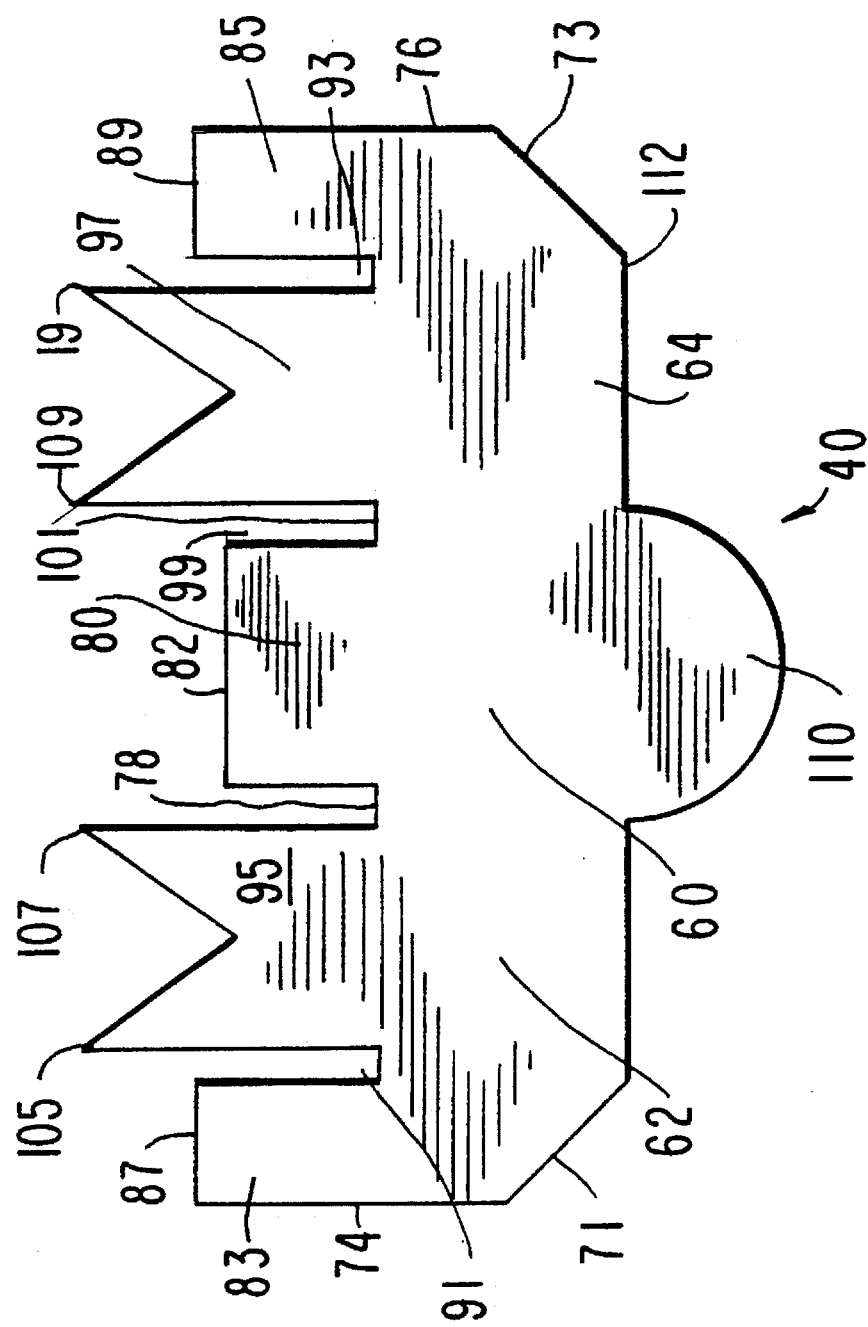
FIG. 9 is a top view of the spring locking clip before being formed into its three-dimensional shape for use in the barrel of the syringe.
Figure 10:
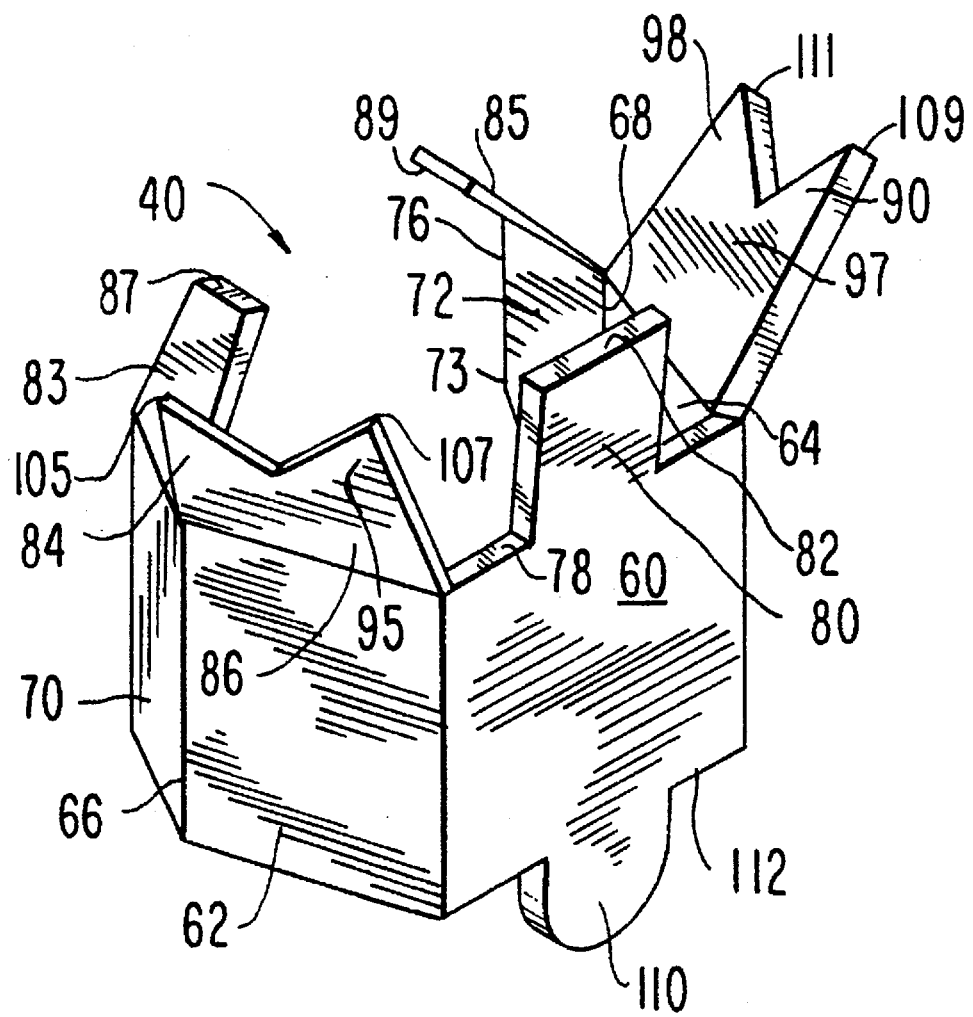
FIG. 10 is a perspective view of the spring locking clip after being formed into shape.
Figure 11:
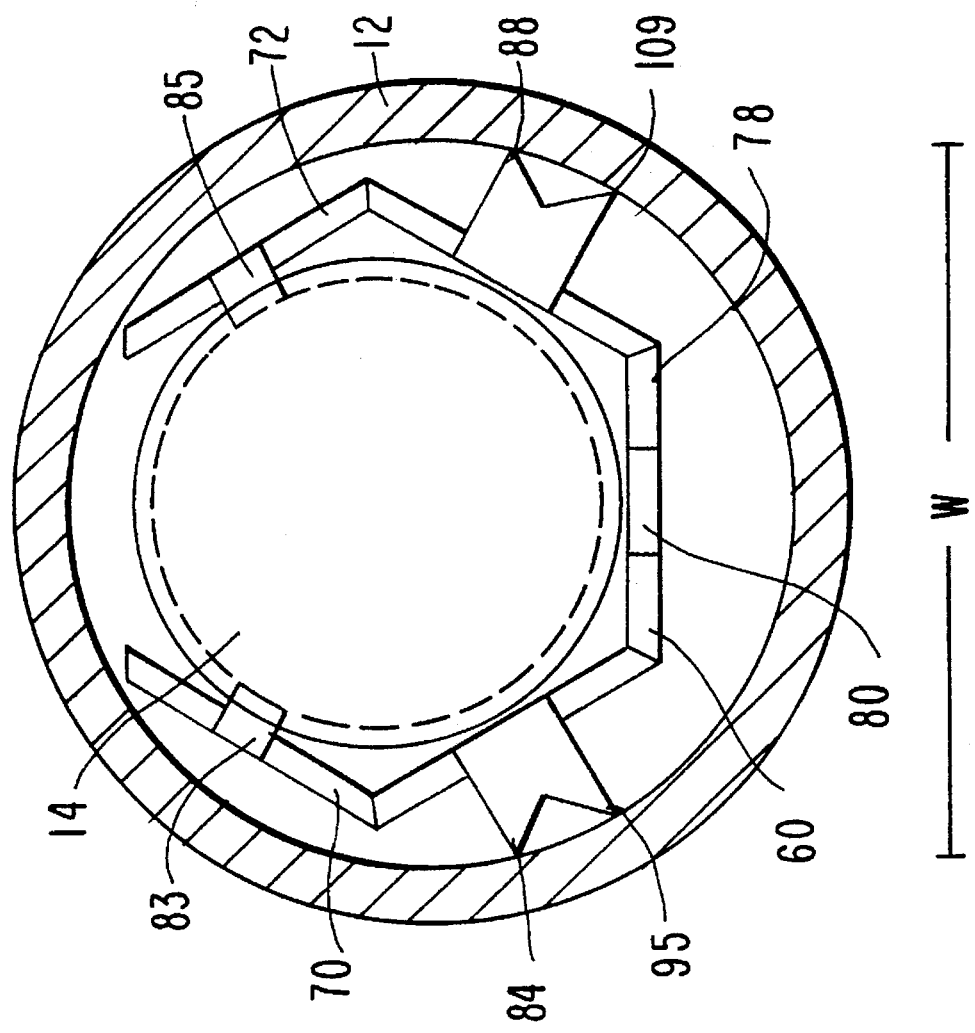
FIG. 11 is a cross section view taken along the lines 11—11 of FIG. 3.

The locking spring 40 is best seen in FIGS. 9, 10 and 11. In the preferred embodiment, when shaped, its basic configuration is that of a hollow six sided figure with one-side open. The overall shape is nearly semi-cylindrical and extends around the plunger about 200°. Preferably, the spring is formed from a thin piece of resilient metal, preferably a single sheet and thickness of stainless steel. The material must be resilient such that it can be spread apart (by the manufacturer) for initial placement around the particular selected ratchet tooth 30 and, yet, after placement on the plunger member, the locking spring 40 springs back toward its original dimensions and configuration. The resiliency also allows the locking spring 40 to flex radially inwardly and outwardly, after securement about the plunger member and receipt within the barrel. The locking clip is installed onto the plunger rod by pressing the open end over a ratchet tooth, thereby temporarily spreading its front walls 70 and 72. After initial placement, the spring member can not become dislodged from the plunger, due to the dimension of the open end of the locking clip in comparison to the diameter D1 of the ratchet teeth of the plunger.

In an alternate version, because of the limited space between the plunger and the inner sidewall 17, occupied by the locking clip 40, the locking clip is secured about the plunger even though it extends less than 180° around the plunger. The dimensioning of the locking spring 40 is such that the distance between the edges of front walls 70 and 72 is less than the diameter D1 of the ratchet teeth. It will be appreciated that the locking spring 40 extends about, in one embodiment, at least 180 degrees of the plunger member 14 such that, after placement, it can not accidentally fall off the plunger member. Indeed, in the preferred embodiment it extends about 200°. As an alternate embodiment, when the syringe is constructed to provide 0.1 cc of medication, the locking clip can be circumferentially smaller. It has been determined that the minimum is about 27° around the plunger.

In a preferred embodiment of the invention, the height h of the locking spring 40 is less than the overall width w, when formed. In this manner the locking spring is more disc-like and is not elongated. It is thus easier and less expensive to manufacture than an elongated device because it requires less material and can be made with high speed manufacturing apparatus. The drawings illustrate the locking spring as extending over about 2 ratchet teeth (See FIGS. 1 and 2) for ease of illustration only. In actual manufacture, however, the height of the locking spring is intended to be less.

The locking spring has a flat back section 60 and a pair of opposed, outwardly extending sidewalls 62 and 64, secured to the side edges of the back section. Extending inwardly from the outermost edges 66 and 68 of sidewalls 62 and 64, respectively, are front walls 70 and 72. Each of back section 60, and sidewalls 62 and 64 are of rectangular configuration. Front walls 70 and 72 have angled edges 71 and 73 respectively (See FIG. 9). The leading vertical edges 74 and 76 of front walls 70 and 72, respectively, are separated by a distance which, as mentioned, is less than the diameter D1 of the base 32 of ratchet teeth 28. In this manner, as mentioned, the locking spring 40, during manufacture of the syringe, can expand outwardly over and around a selected ratchet tooth 30 and, yet, as the leading vertical edges 74 and 76 pass over the diameter D1 of a base 32 of the plunger, the resiliency of the locking spring forces it to reassume its original dimensions. In this manner, the spring will not accidentally fall off or be removed from the plunger member unless physical force is deliberately applied thereto. As mentioned, in the alternate embodiment of the invention where the locking clip is less than 180°, even extending down to about 27° for syringes of 1 cc size capable of delivering dosages as low as 0.1 cc, the locking clip can not be removed from the plunger after insertion into the barrel since the interior space of the barrel is consumed by the plunger and the clip. The clip then has no ability to move away from the plunger. Rather it is sandwiched between inner sidewall 17 and the plunger.

A top edge 78 extends along back section 60. Extending upwardly from top edge 78, basically centered along back section 60, is a tab 80. Tab 80 has an edge 82 configured to be able to touch the outside edge of the base 32 of a ratchet tooth. Tab 80 is coplanar with back section 60. The tab, touching the edge of the plunger teeth, prevents rocking motion of the clip on the plunger during plunger movement and ensures alignment between clip and plunger. The tab prevents jamming.

Proximally and inwardly directed camming teeth 83 and 85 extend upwardly from front walls 70 and 73 respectively. The locking spring 40 when placed on the plunger dangles on the selected ratchet tooth. The inwardly angled camming teeth allow the clip to be moved distally during a delivery stroke. More specifically, they come into contact with the base 32 of the ratchet tooth and the clip is pushed distally as the plunger is moved distally. Gaps 91 and 93 are flexibility control gaps which modify the flexibility of the camming teeth. Top edges 87 and 89 will initially rest on inclined surface 31 of the ratchet tooth. The top edges 87 and 89 will, upon distal movement of the plunger, abut beneath the base of a ratchet tooth so that distal movement of the plunger carries the clip along with the plunger. Yet, the resiliency of the teeth 83 and 85 allows, via radial flexing of the spring, the teeth to cam over and ride on the inclined surfaces 31 of the ratchet teeth of the plunger, as the plunger is moved proximally, when the locking spring is held in its position inside the barrel by the action of the locking teeth 84, 86, 88 and 90 embedding into the inner sidewall 17 of the barrel. The inner side wall 17 of the barrel may be roughened to facilitate the frictional interengagement and embedding of the contact points of the locking teeth of the spring clip therein.

Movement of plunger 14 in the distal direction forces the locking spring to move with it since a base 32 of a ratchet tooth pushes on top edges 87 and 89 of camming teeth 83 and 85. However, the resiliency of locking spring 40 allows for the plunger to move proximally with respect to the held-in-position or stationary locking spring 40 since the camming teeth will cam or ride over inclined surfaces 31.

Extending proximally and outwardly from the top edge of sidewalls 62 and 64 are locking teeth 84, 86, 88 and 90. Locking teeth 84 and 86 extend from sidewall 62 and locking teeth 88 and 90 extend from sidewall 64. The localized sections 95 and 97 carry the locking and embedding teeth 84 86, 88 and 90 and serve to reinforce their action. Flexibility control gaps 99 and 101 provide control to the flexibility of sections 95 and 97. The locking teeth are of triangular configuration and terminate in contact points 105, 107, 109 and 111. The contact points extend outwardly from the outside planar surface of sidewalls 62 and 64 and, indeed, the locking points contact the interior sidewall 17 of the cylinder body 12. They bear against the sidewall. The hardness of the contact points is greater than the hardness of the interior sidewall 17 of the cylinder body 12 such that the contact points will dig and embed into the interior sidewall surface of the cylinder body when the locking spring 40 is attempted to be moved by the plunger in the proximal direction. The radial outward resiliency of the spring embeds the contact points into sidewall 17. When such proximal movement is attempted, the contact points prevent the locking spring from moving proximally. The locking spring can, however, move distally since the contact points radially flex inwardly and will slide over the interior sidewall 17 during plunger movement in the distal direction. The shape and resiliency of the device allows for the discussed radial flexing movement. The distance between contact points 105 or 107, and 109 or 111 may be less than the interior sidewall diameter of the cylinder body 12, and, yet, since the contact points extend outwardly with respect to the outside planar surface of the sidewalls 62 and 64, all contact points 105, 107, 109 and 111 are expected to contact the interior sidewall 17 of the cylinder body 12. The use of multiple contact points ensures embedding of the locking clip, even if there are tolerance irregularities to the inner sidewall 17 of the barrel.

A semicircular tab 110 extends distally from back 60. It counter balances tab 80 and further prevents jamming of the clip during plunger movement. It extends i.e., is bent radially inwardly towards the plunger, at or about edge 112. Tab 110 provides for smooth distal movement of the plunger and clip without scraping the inside of the barrel. When the plunger is fully moved in the distal direction, tab 110 is actually forced between the plunger seal 52 and the sidewall 17 further locking the clip in the distal location.

The construction, manufacture and use of the device is as follows: The cylinder body 12 is formed in the same manner and with the same materials as is currently done in connection with conventional medical syringes. The plunger member 14, with its ratchet teeth and seals 34 and 52, is preferably formed as a single plastic molded product. In the preferred embodiment the plunger is formed from a plastic having an embrittlement additive. The rubber piston 44 is attached to the plunger. The manufacturer determines the maximum dosage for a particular batch of syringes. The manufacturer has a choice, either to down size the spring barrel for a particular maximum dosage and/or adjust the location of the spring locking clip onto the plunger rod to be used in a more standard size syringe. With that maximum dosage in mind, the locking spring 40 will be placed on the ratchet tooth 30 which corresponds to the maximum desired dosage. The individual ratchet teeth can be marked or imprinted during molding with suitable identifying indicia to facilitate the location of the locking spring 40 about the particular ratchet tooth which corresponds to a particular maximum dosage.

Placement of this is accomplished by spreading front walls 70 and 72, camming vertical edges 74 and 76 over base 32. Locating the locking spring 40 toward the distal end of the plunger member 14 provides a smaller maximum dosage for the syringe than locating the same spring member 40 toward the proximal end. During placement of the clip, the edges 74 and 76 of the locking clip physically spread such that the distance between them becomes greater than the diameter D1 of the base 32 of the ratchet teeth. This is accomplished by the resiliency of the spring clip in the radial direction. As so located, the clip is not firmly held against the plunger, but, rather, the camming teeth 83 and 85 touch the inclined surface 31 so that the locking clip dangles from a ratchet tooth.

When the leading edges pass the diameter D1 of the ratchet plunger member, the resiliency of the locking spring forces the edges 74 and 76 to once again assume their original dimension. In this manner, it should be appreciated by those of ordinary skill in the art that the locking spring 40 is located around the plunger member such that the locking spring cannot be easily removed without applying physical force to once again spread apart edges 74 and 76. The locking spring is held on the plunger by the greater than 180° configuration and by the camming teeth 83 and 85 resting on the inclined surface 31 of the ratchet tooth. The locking spring does not grip a ratchet tooth but is loosely held onto the tooth's inclined surface. Top edges 87 and 89 of teeth 83 and 85 are, as mentioned, projected or bent inwardly a sufficient distance such that they bear against and touch the incline 31 of a particular ratchet tooth.

Locking spring 40 can not move proximally with respect to the plunger member 14 since that relative movement is blocked by the mechanical interaction of top edges 87 and 89 of the camming teeth beneath the base of the upwardly adjacent ratchet tooth. With the locking spring located at the position desired, the manufacturer completes the assembly process by securing the plunger member 14 along with the locking spring 40 into the cylinder body or barrel. The resiliency of the spring allows for the plunger and clip to be inserted into the barrel. The article is then packaged and delivered to the end user.

Upon receipt by the user, the syringe 10 is removed from its packaging. In a conventional manner, the needle 15 is inserted into the vial of medication and the thumb-contacting disc 20 moved proximally with respect to finger grip 26. During plunger retraction or proximal movement, locking spring 40 will remain fixed in the barrel, a consequence of outward radial flexing of the locking spring thereby embedding the teeth into the sidewalls. The plunger can move proximally until the top edge of seal 52 contacts the bottom edge 112 of the locking spring 40. Once this abutment occurs, further proximal movement of the plunger member 14 can not happen since the contact points 105, 107, 109 and 111 of the locking teeth 84, 86, 88 and 90 are physically dug into the interior sidewall 17 of the cylinder body 12.

It should be appreciated by those of ordinary skill in the art that the locking spring 40 cannot move when the plunger member 14 is proximally moved. The contact points prevent any proximal movement of the locking spring. Initial location of the locking spring and thus locking teeth 84, 86, 88 and 90 with respect to the plunger determines the maximum amount of relative reciprocation of the plunger in the barrel and thus the maximum dosage which can be administered by the syringe. During proximal plunger movement, the tab 80 and tab 110 of the locking spring glide or cam over the edges of the ratchet teeth. Together they maintain alignment and prevent jamming of the device. As plunger member 14 is withdrawn or moved proximally with respect to cylinder body 12, the radial resiliency of the teeth of locking spring 40 is such that the edges 87 and 89 will travel over each inclined surface 31 of each ratchet tooth 30. Since the locking spring is maintained within the cylinder body 12 in relative position by the interaction of the contact points 105, 107, 109 and 111 against the inside cylindrical surface 17 of the cylinder body 12, the plunger member 14 can be fully withdrawn until seal section 52 contacts the bottom edge 112 of the locking spring 40. When this occurs, however, further proximal movement of the plunger member 14 is mechanically blocked since further desired proximal movement of the plunger will only further embed the contact points into the inner sidewall 17 of the cylinder body 12. Thus, the plunger member is restricted by its relative movement with respect to the cylinder body.

With the medication now contained within the cylinder body 12, more specifically, between piston 44 and the tip 18 of cylinder body 12, the user is ready to dispense the medication through needle 15, as and when desired. The needle is inserted through the patient's skin and the user then applies pressure onto thumb-contacting disc 20 such that plunger member 14 is moved distally, thereby pushing piston 44 distally and, thereby, dispensing all medication through tip 18 and needle 15. Since top edges 87 and 89 of camming teeth 83 and 85 will be pushed distally by contact with the base 32 of the above-located ratchet tooth, the locking spring 40 will flex radially inwardly and slide distally within the barrel, as plunger member 14 is distally moved to dispense medication. The contact points only prevent proximal movement of the locking spring; distal movement is allowed by the sliding of the contact points along the interior sidewall and the inherent resiliency of the locking clip.

After all medication has been dispensed from the syringe, the seal 52, above piston 44, abuts against the bottom edge 112 of the locking clip. A second reciprocation of the plunger member 14 with respect to cylinder body 12 is mechanically blocked since locking spring 40, adjacent to the seal 52 will embed into the sidewall 17 as the plunger is attempted to be moved proximally. It is prevented from a second proximal movement by contact points 105, 107, 109 and 111 digging into the interior sidewall 17 of the cylinder body 12. Thus, it should be apparent, that a second reciprocation, to draw medication or drugs into the syringe 10, is mechanically blocked since the plunger member 14 cannot move a second time in the proximal direction with respect to cylinder body 12.

To further disable the syringe 10 for subsequent potential use, the user can, if desired, bend or twist the thumb-contacting disc 20 along the fracture plane 24, until it breaks apart. Without the thumb-contacting disc 20 secured to the plunger member 14, it is far more difficult to reciprocate the plunger member 14, in either direction, even assuming that one could first disable the locking spring mechanism. Furthermore, the thumb-contacting disc 20 can now serve as a means to limit syringe distribution. For example, a certain number of such discs may be collected and turned into the manufacturer or dispenser in exchange for a like number of new syringes. Inventory and audit control are easier to keep track of with the flat discs than with the entire bulky syringes.

Figure 12:
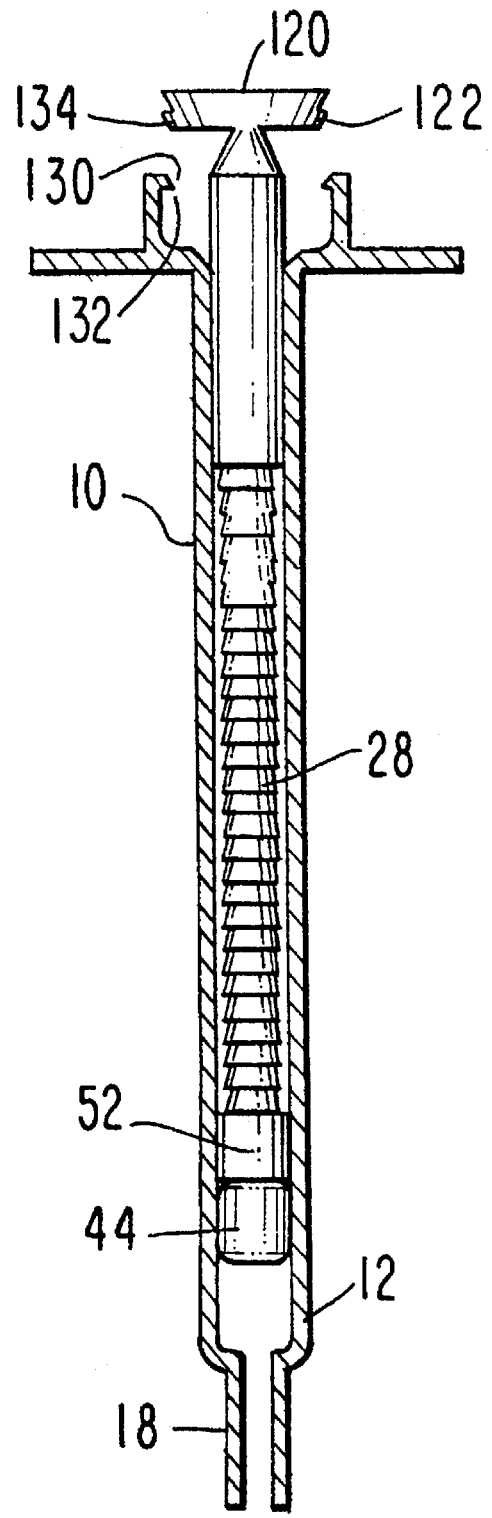
FIG. 12 is a side cross-sectional view of an alternate embodiment of the barrel, plunger and thumb-engaging disc portion of the plunger.

In an alternate embodiment of the present invention, the thumb-contacting disc is provided (see FIG. 12) with an inclined thumb section 120, and a second, inclined outer wall disc-like section 122. Together these comprise an annular male dove-like arrangement for the plunger. The proximal portion of the cylinder body 12, adjacent the finger grip 26, is provided with an annular inwardly directed edge 130, terminating in a locking lip 132. Together these comprise an annular female, dove-tail like arrangement for the barrel. Thus, when the thumb-contacting disc 120 is fully reciprocated in the distal direction, inclined outer wall 122 slides until the locking lip 132 will overlap the second annular disc-like section 122, thereby preventing any further proximal or distal movement of the plunger with respect to the cylinder body 12. Thus, it should be appreciated and apparent to those of ordinary skill in the art that the smallest diameter of the edge 130, at the point of locking lip 132, is less than the largest diameter of edge surface 134, although the resiliency of the barrel and a split at the proximal end allows edge 130 to cam over edge 134 until held by locking lip 132.

In an alternate embodiment of the invention, a mechanism is provided to thwart tampering with the locking mechanism. After the first full distal movement of the plunger, the locking clip is embedded into the sidewall of the syringe, adjacent to seal 52. The distal force needed to overcome the force of the locking clip being embedded into the sidewall of the barrel exceeds the tensile strength of the plunger such that a second attempted proximal movement will result in a physical separation of the plunger along its length, preferably just above the locking clip (see FIG. 4). To localize severing at that location, a reduced diameter section 114 of the plunger is located above the seal section 52. In the preferred embodiment the reduced cross-sectional area of the plunger is located so that the break will occur just above the proximal surface of the clip. As seen in FIGS. 6, 7 and 8, two or more reduced areas 114 and 116 are provided as potential areas to be severed by the movement of the plunger.

As best seen in FIG. 11 the radial resiliency and strength of the locking clip actually moves and forces the plunger out of axial alignment with the axis of the barrel. Thus, in very small diameter and volume syringes, a locking clip can be provided which still functions to block reuse. Only single thickness of metal across a diameter of the barrel is required between the plunger and the sidewall of the barrel. In an alternate embodiment, because the clip is not acting symmetrically around the plunger but, rather, asymmetrically, the locking clip can be made as small as about 27° of the 360° plunger. In this manner, very small capacity syringes with a locking non-reusable mechanism can be achieved. The vector forces of the locking teeth push the plunger out of alignment.

There have been described several embodiments of a single-use hypodermic needle and syringe assembly. While the invention has been described with reference to specific embodiments, the description is illustrative of the invention and is not to be construed as limiting the invention. Various modifications and applications may occur to those skilled in the art without departing from the true spirit and scope of the invention.

We claim:

1. A single-use syringe comprising:

a hollow barrel having a proximal end and a distal end and having an interior cylindrical sidewall extending therebetween, and a needle holding means at said distal end of said barrel;

a basically cylindrical plunger rod having a longitudinal axis located within said barrel for axial movement of said plunger rod therein for drawing fluid into and expelling fluid out of said barrel through said needle holding means, said plunger rod extending beyond said proximal end of said barrel and having a sealing and expelling fluid piston adjacent a distal and of said plunger, said plunger rod having a plurality of frustoconical ratchet teeth;

a radially resilient, locking spring clip with a circumferential opening mounted on said plunger rod, said locking spring clip having plunger rod engaging means and at least one, outwardly-directed sidewall, locking tooth having a contact point directed toward said proximal end in contact with said sidewall, said plunger rod engaging means contacting said plunger rod and being mechanically linked to said ratchet teeth to move said spring clip along with said plunger rod where said plunger rod is moved toward said distal end and, yet, said spring clip radially expands over said ratchet teeth when said plunger rod is moved toward said proximal end, thereby holding in relative place with respect to said sidewall, a consequence of said contact point frictionally engaging said sidewall, said plunger rod being free to move a first time toward said proximal end of said barrel, said locking spring clip being then held in relative sidewall position by the frictional engagement of said contact point against said sidewall as said plunger rod moves toward said proximal end and, yet, movement of said plunger rod towards said distal end of said barrel causes said plunger engaging means to move said locking spring clip along with said plunger rod toward said distal end;

whereby said plunger rod, barrel and locking spring clip permits the barrel of said syringe to draw fluid, the volume of said barrel being defined by the predetermined initial location of said locking spring clip on said plunger rod, by movement of said plunger rod toward said proximal end, said opening of said spring clip serving to allow radial flexing and camming of said spring clip over said ratchet teeth thereby facilitating the relative movement of said plunger rod with respect to said spring clip, and, movement of said plunger rod toward said distal end expels said fluid through said needle tip holding means; and a second movement of said plunger rod toward said proximal end is prevented by frictional engagement between said contact point and said sidewall.

2. A single-use syringe as claimed in claim 1 wherein said plunger engaging means comprises an inwardly directed camming tooth configured to slide over the surfaces of said ratchet teeth of said plunger rod when said plunger rod is moved toward said proximal end and said camming tooth of said spring clip mechanically interacts with one of said ratchet teeth of said plunger rod to move said spring clip with said plunger rod when said plunger rod is moved toward said distal end.

3. A single-use syringe as claimed in claim 1 wherein said locking spring clip extends about 200° around said plunger rod.

4. A single-use syringe as claimed in claim 1 wherein said locking spring clip extends less than 180° around said plunger rod.

5. A single-use syringe as claimed in claim 1 wherein said locking spring clip extends less than 18° and more than about 27° around said plunger rod.

6. A single-use syringe as claimed in claim 1 wherein said locking spring clip forces said plunger rod out of axial alignment with respect to said hollow barrel.

7. A single-use syringe as claimed in claim 1 wherein the distance between said axis of said locking spring clip and said contact point, when said locking spring is not compressed by contact with said sidewall is slightly greater than the radius of said interior cylinder sidewall.

8. A single-use syringe as claimed in claim 1 wherein said plunger rod is provided with sealing means to prevent unauthorized access to said ratchet teeth and said locking spring clip.

9. A single-use syringe as claimed in claim 8 wherein the limit of movement of said plunger rod towards said proximal end is controlled by physical abutment between said sealing means and said locking spring clip.

10. A single-use syringe as claimed in claim 1 wherein said locking spring clip flexes radially outwardly over the surfaces of said ratchet teeth during movement of said plunger rod toward said proximal end.

11. A single-use syringe as claimed in claim 1 wherein sealing means is provided at both the distal end and the proximal end of said plunger rod to prevent unauthorized access to said ratchet teeth and said locking spring clip.

12. A single-use syringe as claimed in claim 1 wherein said locking spring clip is multi-sided.

13. A single-use syringe as claimed in claim 1 wherein the dimension of said opening is less than the larger diameter of said ratchet teeth.

14. A single-use syringe as claimed in claim 1 wherein said sidewall is roughened.

15. A single-use syringe as claimed in claim 1 wherein said plunger rod is provided with at least one reduced diameters region, less than either the diameter of said ratchet teeth.

16. A single-use syringe as claimed in claim 15 wherein said reduced diameter region is located in close proximity to said piston.

17. A single use syringe as claimed in claim 15 wherein said reduced diameter region is located towards the distal end of said locking clip after said plunger rod has been moved towards said distal end of said barrel.

18. A single-use syringe as claimed in claim 1 wherein two or more contact points are provided to said locking spring clip.

19. A single-use syringe as claimed in claim 1 wherein said locking spring clip is provided with an alignment tab riding over the surfaces of said ratchet teeth, for ensuring that said locking spring clip does not jam during movement of said plunger rod toward said proximal end.

20. A single-use syringe as claimed in claim 1 wherein the tensile strength of said plunger rod is less than frictional force embedding said contact point of said locking spring clip into said sidewall.

21. A single-use syringe as claimed in claim 1 wherein said ratchet teeth are marked with dosage indicating means.

22. A single-use syringe as claimed in claim 1 wherein any diameter of said barrel intersects no more than a single thickness of said spring clip.

23. A single-use syringe as claimed in claim 1 wherein said locking spring comprises an open ended hexagonal shape with said opening being less than the diameter of the base of said ratchet teeth.

24. A single-use syringe as claimed in claim 1, further comprising an alignment tab centrally located on said locking spring clip and at least one opposed pair of contact points located on both sides of said alignment tab.

25. A single-use syringe as claimed in claim 1 wherein the thickness of material of said spring locking clip, across all diameters of said barrel, is only a single thickness.

26. A single-use syringe as claimed in claim 1 wherein said locking spring clip is further provided with an alignment and anti-jamming means comprising a first tab extending toward said distal end and an inwardly directed second tab directed toward said proximal end.

27. A single-use syringe as claimed in claim 26 wherein said second tab is nearly semi-circular.

* * * * *